United States Patent [19]

Sandermann et al.

[11] 4,087,540
[45] May 2, 1978

[54] OCTAHYDRO-N-[(TRICHLOROMETHYL)-THIO]-NAPHTHALENEDICARBOXIMIDES

[75] Inventors: Wilhelm Sandermann, Donaustauf; Heinz Eggensperger, Hamburg; Karl-Heinz Diehl, Norderstedt, all of Germany

[73] Assignee: Sterling Drug Inc., New York, N.Y.

[21] Appl. No.: 782,752

[22] Filed: Mar. 30, 1977

[51] Int. Cl.² .................. C07D 209/66; A61K 31/40
[52] U.S. Cl. .................. 424/274; 260/326 C; 260/326 H; 260/346.3
[58] Field of Search .................. 260/326 C, 326 H; 424/274

[56] References Cited

U.S. PATENT DOCUMENTS

| 2,553,770 | 5/1951 | Killleson | 260/326 H |
| 3,452,045 | 6/1969 | Roberts et al. | 260/326 C |

FOREIGN PATENT DOCUMENTS

| 40/21620 | 9/1965 | Japan | 260/326 H |
| 255,933 | 3/1971 | U.S.S.R. | 260/326 H |

*Primary Examiner*—Donald G. Daus
*Assistant Examiner*—Mark L. Berch
*Attorney, Agent, or Firm*—Frederik W. Stonner; B. Woodrow Wyatt

[57] ABSTRACT

The invention relates to 1,2,3,5,6,7,8,8a-octahydro-4,7-dimethyl-N-[(trichloromethyl)thio]-1,2-naphthalenedicarboximide, 1,2,3,4,4a,5,6,7-octahydro-2,2-dimethyl-N-[(trichloromethyl)thio]-1,3-methanonaphthalene-5,6-dicarboximide, and 1,2,3,4,5,6,7,8-octahydro-5,5-dimethyl-N-[(trichloromethyl)thio]-2,3-naphthalenedicarboximide having fungicidal activity, to fungicidal compositions containing them, and to methods for their use.

12 Claims, No Drawings

OCTAHYDRO-N-[(TRICHLOROMETHYL)THIO]-NAPHTHALENEDICARBOXIMIDES

BACKGROUND OF THE INVENTION

1. Field of the Invention

The invention relates to octahydro-N-[(trichloromethyl)thio]naphthalenedicarboximides having fungicidal activity which are represented by the general formula

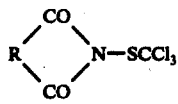
  I where R represents

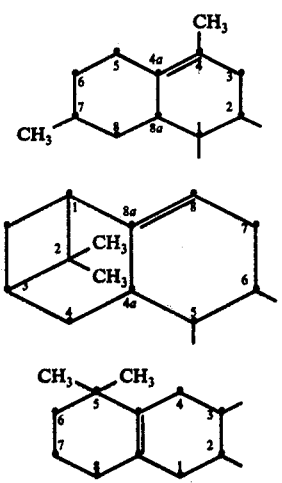

The compounds represented by formula IA, IB and IC respectively are 1,2,3,5,6,7,8,8a-octahydro-4,7-dimethyl-N-[(trichloromethyl)-thio]-1,2-napthalenedicarboximide; 1,2,3,4,4a,5,6,7-octahydro-2,2-dimethyl-N-[(trichloromethyl)thio]-1,3-methanonaphthalene-5,6-dicarboximide; and 1,2,3,4,5,6,7,8-octahydro-5,5-dimethyl-N-[(trichloromethyl)thio]-2,3-naphthalenedicarboximide.

The invention further relates to fungicidal compositions containing, and to the method of use of, compounds of the formulas IA, IB and IC.

2. Description of the Prior Art

Fungicidal compounds have been employed to combat fungus infections in man and animals, as plant protectants and for the preservation of materials such as wood, leather, and paper. One of the most important applications is in wood preservation, e.g., preservation of boards against blue discoloration and of building timbers against fungus destruction. Fungicides find increasing application in the preservation of paints against primary and secondary fungal attack, e.g., when applied to wooden window frames, and wooden walls in dairies, bakeries and cellars.

Known fungicides are organic mercury compounds, organic tin compounds, pentachlorophenol and dithiocarbamic acid derivatives. Many of these compounds, however, suffer from disadvantages. For example, mercury compounds are very toxic. The organic tin compounds undergo changes under the influence of light and quickly lose their activity. Pentachlorophenol is very volatile and per se, as well as due to accompanying impurities, is very toxic so that its use is banned in several countries. Finally, derivatives of dithiocarbamic acid have the disadvantage that in contact with metals or metal salts such as siccatives, they cause discoloration.

The trichloromethylthio compounds described in U.S. Patent 2,533,770 are good, long acting fungicides whose action is due to the blocking of SH-groups in phosphorylating enzymes, cf, R. G. Owens and H. M. Novotny, Contr. Boyce Thompson Inst., vol. 20, p. 171 (1959). These fungicides are prepared by the reaction of the appropriate dicarboxylic acid imide with trichloromethanesulfenyl chloride. The imides employed as starting materials in this reaction are endomethylenetetrahydrophthalimide, phthalimide, tetrahydrophthalimide and succinimide. Of the compounds prepared, primarily compounds represented by the formulas II and IV below are encountered as items of trade.

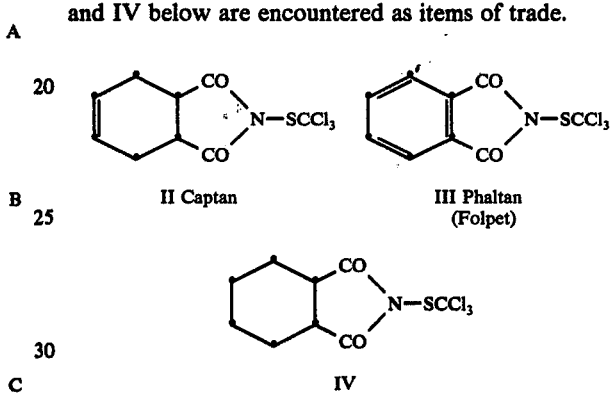

II Captan   III Phaltan (Folpet)

IV

In addition, fluorinated compounds having formulas V and VI below have been developed which display useful properties as fungicidal additives to paints, cf. "Fette, Seifen, Anstrichmittel", vol. 68 (1966) pp. 275-279.

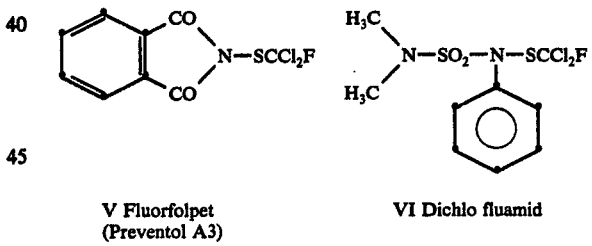

V Fluorfolpet (Preventol A3)   VI Dichlo fluamid

The foregoing identified trichloromethylthio compounds, while being weather-resistant, [cf. B. A. Richardson, B.W.P.A. Annual Convention (1972), Chapter (6), Sapstain Control, P. 9] are very poorly soluble which impairs their fungicidal activity. Thus, Captan (II), owing to its low solubility in paints, is practically ineffective, cf. B. A. Richardson, loc. cit. The solubility of compound IV in petroleum ether is only 0.3%. The low solubility of these compounds makes the preparation of effective fungicidal agents extremely difficult since in order to obtain sufficient activity, the agent should on the average contain about 3% of the active ingredient. Thus, E. Hoffman and A. Saracz found that 1% of compound III is insufficient to prevent blue discoloration, 2 to 3% being required [J. Oil Col. Chem. Assoc., vol. 50 (1967) p. 434].

In order to find a fungicide with high solubility in petroleum hydrocarbons, numerous N-trichloromethylthio compounds have been synthesized and tested for activity and solubility. In these investigations it was found that not all compounds represented by the general formula

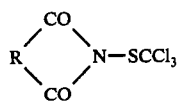

are active fungicides as disclosed in U.S. Pat. No. 2,553,770. Rather, activity is associated with certain structural features. Thus, the N-trichloromethylthio compounds prepared from anthracene-maleic anhydride adduct, homophthalic anhydride, caryophyllene-maleic anhydride adduct, isoeugenol-maleic anhydride adduct, camphoric anhydride, hexadecylsuccinic anhydride, and many other anhydrides are inactive.

SUMMARY OF THE INVENTION

In the compound aspect of the invention there is provided a compound selected from the group consisting of 1,2,3,5,6,7,8,8a-octahydro-4,7-dimethyl-N-[(trichloromethyl)-thio]-1,2-naphthalenedicarboximide; 1,2,3,4,4a,5,6,7-octahydro-2,2-dimethyl-N-[(trichloromethyl)thio]-1,3-methanonaphthalene-5,6-dicarboximide; and 1,2,3,4,5,6,7,8-octahydro-5,5-dimethyl-N-[(trichloromethyl)thio]-2,3-naphthalenedicarboximide which are represented by the structural formulas IA, IB and IC respectively hereinabove.

The compounds of the invention represented by formulas IA, IB and IC were found to have excellent fungicidal activity and good solubility in petroleum hydrocarbons.

In a composition aspect of the invention there is provided a fungicidal composition comprising as active ingredient a compound selected from the group consisting of the compounds represented by structural formulas IA, IB and IC above, and mixtures of said compounds, and a carrier therefor.

In a method aspect of the invention there is provided a method for preventing or retarding the deleterious effects associated with fungus contamination on a material susceptible to fungus contamination which comprises treating the material with a fungicidally effective amount of a compound selected from the group of the compounds represented by formulas IA, IB and IC above, and mixtures of said compounds.

DETAILED DESCRIPTION INCLUSIVE OF THE PREFERRED EMBODIMENTS

The compounds of structural formulas IA, IB and IC are prepared using known procedures. Thus an anhydride represented by the general structural formula

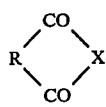

VII where X represents oxygen (O) and R has the same meaning disclosed hereinabove for formula I, is heated with ammonium hydroxide to give the corresponding imide of structural formula VII (X=NH), the sodium salt of which is then treated in a suitable solvent, such as dioxane, benzene, an alcohol, or water, with trichloromethanesulfenyl chloride to give compound I. The anhydrides VII (X=O) where R represents the radicals A and B disclosed hereinabove are known compounds which are prepared by Diels-Alder reaction of maleic anhydride and respectively dipentene [see Ullman, Encyclopedia of Technical Chemistry, 3rd. Edition, Vol. 17, 62 (1966)] and nopadiene [see G. Ohloff and G. Schade, Angew. Chem. 67, 427 (1955)]. Anhydride VII (X=O) where R represents the radical C disclosed hereinabove is prepared by Diels-Alder reaction of myrcene and maleic anhydride and cyclization, e.g., with an appropriate acid or boron trifluoride, of the resulting 1,2,3,6-tetrahydro-4-(4-methyl-3-pentenyl)phthalic anhydride represented by the structural formula

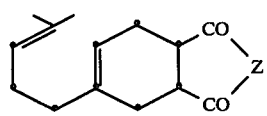

VIII where Z represents oxygen (O) [see O. Diels and K. Alder, Liebigs Annalen 470, 62 (1929); R. Enninga and G. J. Beets, British Specification No. 881,535].

By substituting maleimide for maleic anhydride in the Diels-Alder reactions described above, the corresponding imides can be directly obtained.

The starting materials dipentene, nopadiene and myrcene are readily obtainable from oil of turpentine, a product of pine resin, or from a by-product of the wood pulp industry (sulfated oil of turpentine).

As noted hereinbefore, the compounds of the invention represented by structural formula I have good solubility in petroleum hydrocarbons and are very active fungicides. These properties appear to be associated with the octahydronaphthalene structure of the compounds. Thus when the anhydride VIII (Z=O) was converted to the corresponding N-[(trichloromethyl)-thio]-imide (VIII, Z=N—S—CCl$_3$) the surprising observation was made that the cyclized compound IC has about five times the fungicidal activity, and against *staphylococcus aureus* about 100 times the activity, of the uncyclized compound VIII (Z=N—S—CCl$_3$) and that the latter compound had only one-fifth the solubility of compound IC. The solubility data and minimum inhibitory concentration against several microorganisms for these two compounds as well as the known fungicide Captan are presented in the following table.

| Compound | Solubility in mineral spirits | Minimum Inhibitory Concentration (%) Microorganism | | | | | | |
|---|---|---|---|---|---|---|---|---|
| | | 1 | 2 | 3 | 4 | 5 | 6 | 7 |
| VIII (X=N—S—CCl$_3$) | 0.6 | 1 | 0.005 | 0.01 | 0.005 | 0.005 | 0.005 | 0.01 |
| IC | 3 | 0.01 | 0.001 | 0.01 | 0.001 | 0.001 | 0.001 | 0.001 |
| Captan | almost insoluble | 0.05 | 0.01 | 0.05 | — | 0.005 | — | 0.01 |

|  | Solubility in mineral | Minimum Inhibitory Concentration (%) Microorganism | | | | | | |
| --- | --- | --- | --- | --- | --- | --- | --- | --- |
| Compound | spirits | 1 | 2 | 3 | 4 | 5 | 6 | 7 |

1 *Staphylococcus aureus*
2 *Penicillium glaucum*
3 *Aspergillus niger*
4 *Sclerophoma pityophila*
5 *Pullularia pullulans*
6 *Saccharomyces cerevisiac*
7 *Candida albicans*

Preparation of the Compounds of the Invention

EXAMPLE 1

1,2,3,4,5,6,7,8-Octahydro-5,5-dimethyl-N-[(trichloromethyl)thio]-2,3-naphthalenedicarboximide (IC)

1,2,3,6-tetrahydro-4-(4-methyl-3-pentenyl)phthalic anhydride (VIII, Z=O) (1000g) and boron trifluoride etherate (100 g.) in 1 liter of benzene was refluxed for one and one-half hours. Work-up, using standard techniques, gave in almost quantitative yield crude 1,2,3,4,5,6,7,8-octahydro-5,5-dimethyl-2,3-naphthalenedicarboxylic acid anhydride (VII, X=O; R is the radical C). The cyclized anhydride (1 mole) was heated slowly to 250° C. with 200 ml. of ammonium hydroxide (s.g. 0.91) until ammonia no longer was liberated, using a condenser of a length which allowed ready evaporation of water. The resulting 1,2,3,4,5,6,7,8-octahydro-5,5-dimethyl-2,3-naphthalenedicarboximide (VII, X=NH; R is the radical C) was dissolved in 500 ml. of 2N sodium hydroxide in ethyl alcohol with warming, the solution was evaporated to dryness in vacuo, and the resulting sodium salt of the imide was suspended in 500 ml. of dioxane and treated with trichloromethanesulfenyl chloride (1.1 moles) in 200 ml. of dioxane with gentle stirring. The reaction was completed by heating at 80° C. for thirty minutes. The mixture was allowed to stand overnight, concentrated in vacuo, and the residue was crystallized from ethyl alcohol (or benzene) to give a yield of 91% of the title compound.

By using procedures similar to those described in Example 1, 1,2,3,5,6,7,8,8a-octahydro-4,7-dimethyl-N-[(trichloromethyl)thio]-1,2-naphthalenedicarboximide (IA) (m.p. 163° C.) and 1,2,3,4,4a, 5,6,7-octahydro-2,2-dimethyl-N-[(trichloromethyl)thio]-1,3-methanonaphthalene-5,6-dicarboxide (IB) ($n_D$=1.5348) were obtained respectively from 1,2,3,5,6,7,8,8a-octahydro-4,7-dimethyl-1,2-naphthalenedicarboximide (VII,X=NH and R represents the radical A) in turn obtained from 1,2,3,5,6,7,8,8a-octahydro-4,7-dimethyl-1,2-naphthalenedicarboxylic acid anhydride (VII, X=O and R represents the radical A); and 1,2,3,4,4a, 5,6,7-octahydro-2,2-dimethyl-1,3-methanonaphthalene-5,6-dicarboximide (VII, X=NH and R represents the radical B) in turn obtained from 1,2,3,4,4a, 5,6,7-octahydro-2,2-dimethyl-1,3-methanonaphthalene-5,6-dicarboxylic acid anhydride (VII, X=O and R represents the radical B).

The compounds of the invention of general formula I are active as fungicides and have good solubility in petroleum hydrocarbons. They are useful for application to and incorporation in materials to retard or prevent fungus growth which cause deterioration of such materials. For example they may be used to prevent or retard the deleterious effects due to fungus growth on wood, leather and paper and in oil-base paints and may also have application as plant protectants.

The compounds of the invention can be prepared for use using conventional techniques. Thus they can be mixed with a suitable carrier, e.g., a solid carrier such as but not limited to clay, talc and bentonite; or with a suitable liquid carrier, e.g., as a solution in a solvent such as but not limited to petroleum hydrocarbons and alcohol, and as suspensions in a non-solvent.

The amounts of the compounds or mixtures thereof to be applied in order to be fungicidally effective will vary depending on a number of factors, for example, on the nature of the material to be protected, and can readily be determined by one having ordinary skill in the art.

We claim:

1. A compound selected from the group consisting of 1,2,3,5,6,7,8,8a-octahydro-4,7-dimethyl-N-[(trichloromethyl)thio]-1,2-naphthalenedicarboximide, 1,2,3,4,4a,5,6,7-octahydro-2,2-dimethyl-N-[(trichloromethyl)thio]-1,3-methanonaphthalene-5,6-dicarboximide, and 1,2,3,4,5,6,7,8-ocatahydro-5,5-dimethyl-N-[(trichloromethyl)thio]-2,3-naphthalenedicarboximide.

2. The compound 1,2,3,5,6,7,8,8a-octahydro-4,7-dimethyl-N-[(trichloromethyl)thio]-1,2-naphthalenedicarboximide according to claim 1.

3. The compound 1,2,3,4,4a,5,6,7-octahydro-2,2-dimethyl-N-[(trichloromethyl)thio]-1,3-methanonaphthalene-5,6-dicarboximide according to claim 1.

4. The compound 1,2,3,4,5,6,7,8-octahydro-5,5-dimethyl-N-[(trichloromethyl)thio]-2,3-naphthalenedicarboximide according to claim 1.

5. A fungicidal composition comprising as active ingredient a fungicidally effective amount of a compound selected from the group consisting of 1,2,3,5,6,7,8,8a-octahydro-4,7-dimethyl-N-[(trichloromethyl)-thio]-1,2-naphthalenedicarboximide, 1,2,3,4,4a,5,6,7-octahydro-2,2-dimethyl-N-[(trichloromethyl)thio]-1,3-methanonaphthalene-5,6-dicarboximide, and 1,2,3,4,5,6,7,8-octahydro-5,5-dimethyl-N-[(trichloromethyl)thio]-2,3-naphthalenedicarboximide, and mixtures of said compounds, and a carrier therefor.

6. A composition according to claim 5 wherein the active ingredient is 1,2,3,5,6,7,8,8a-octahydro-4,7-dimethyl-N-[(trichloromethyl)thio]-1,2-naphthalenedicarboximide.

7. A composition according to claim 5 wherein the active ingredient is 1,2,3,4,4a,5,6,7-octahydro-2,2-dimethyl-N-[(trichloromethyl)thio]-1,3-methanonaphthalene-5,6-dicarboximide.

8. A composition according to claim 5 wherein the active ingredient is 1,2,3,4,5,6,7,8-octahydro-5,5-dimethyl-N-[(trichloromethyl)thio]-2,3-naphthalenedicarboximide.

9. A method for preventing or retarding the deleterious effects associated with fungus contamination on a material susceptible to fungus contamination which comprises treating the material with a fungicidally effective amount of a compound selected from 1,2,3,5,6,7,8,8a-octahydro-4,7-dimethyl-N-[(trichloromethyl)thio]-1,2-naphthalenedicarboximide, 1,2,3,4,4a,5,6,7-octahydro-2,2-dimethyl-N-[(trichloromethyl)-thio]-1,3-methanonaphthalene-5,6-dicarboximide, and 1,2,3,4,5,6,7,8-octahydro-5,5-dimethyl-N-[(trichloromethyl)thio]-2,3-naphthalenedicarboximide.

10. A method according to claim 9 wherein the compound is 1,2,3,5,6,7,8,8a-octahydro-4,7-dimethyl-N-[(trichloromethyl)thio]-1,2-naphthalenedicarboximide.

11. A method according to claim 9 wherein the compound is 1,2,3,4,4a,5,6,7-octahydro-2,2-dimethyl-N-[(trichloromethyl)thio]-1,3-methanonaphthalene-5,6-dicarboximide.

12. A method according to claim 9 wherein the compound is 1,2,3,4,5,6,7,8-octahydro-5,5-dimethyl-N-[(trichloromethyl)thio]-2,3-naphthalenedicarboximide.

* * * * *

UNITED STATES PATENT OFFICE
CERTIFICATE OF CORRECTION

Patent No. 4,087,540　　　　　　　　　　Dated　May 2, 1978

Inventor(s)　Wilhelm Sandermann et al.

It is certified that error appears in the above-identified patent and that said Letters Patent are hereby corrected as shown below:

On the cover sheet insert Foreign Application Priority Data:

-- Germany　　2,614,936　　　　April 7, 1976 --.

Signed and Sealed this

Twenty-third Day of January 1979

[SEAL]

Attest:

RUTH C. MASON
*Attesting Officer*

DONALD W. BANNER
*Commissioner of Patents and Trademarks*